(12) United States Patent
Cholody et al.

(10) Patent No.: US 6,664,263 B2
(45) Date of Patent: Dec. 16, 2003

(54) 1,8-NAPHTHALIMIDE IMIDAZO{4,5,1-DE}ACRIDONES WITH ANTI-TUMOR ACTIVITY

(75) Inventors: Wieslaw M. Cholody, Frederick, MD (US); Teresa Kosakowska-Cholody, Frederick, MD (US); Christopher J. Michejda, North Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/221,236

(22) PCT Filed: Mar. 5, 2001

(86) PCT No.: PCT/US01/07087

§ 371 (c)(1),
(2), (4) Date: Mar. 3, 2003

(87) PCT Pub. No.: WO01/66545

PCT Pub. Date: Sep. 13, 2001

(65) Prior Publication Data

US 2003/0203916 A1 Oct. 30, 2003

Related U.S. Application Data

(60) Provisional application No. 60/187,991, filed on Mar. 7, 2000.

(51) Int. Cl.⁷ .................... A61K 31/473; A61K 31/496; C07D 401/12; C07D 401/14
(52) U.S. Cl. .......... 514/288; 546/66; 544/361; 544/333; 514/253; 514/256
(58) Field of Search .............. 514/288, 253, 514/256; 546/66; 544/361, 333

(56) References Cited

U.S. PATENT DOCUMENTS

5,789,418 A    8/1998   Keilhauer et al.
6,187,775 B1 * 2/2001   Michejda et al. ...... 514/253.02

FOREIGN PATENT DOCUMENTS

EP    0 502 668    9/1992
WO    97/38999    10/1997

* cited by examiner

*Primary Examiner*—C. S. Aulakh
(74) *Attorney, Agent, or Firm*—Peter F. Corless; Christine C. O'Day; Edwards & Angell, LLP

(57) ABSTRACT

The invention provides imidazoacridone compounds of general formula (1) which have cytotoxic and anti-tumor activity. The invention also provides methods of preparing the compounds, and methods of using the compounds for the treatment of cancer or other mammalian diseases characterized by undesirably high levels of cell proliferation. The compounds of the invention are also expected to have utility as research tools.

(1)

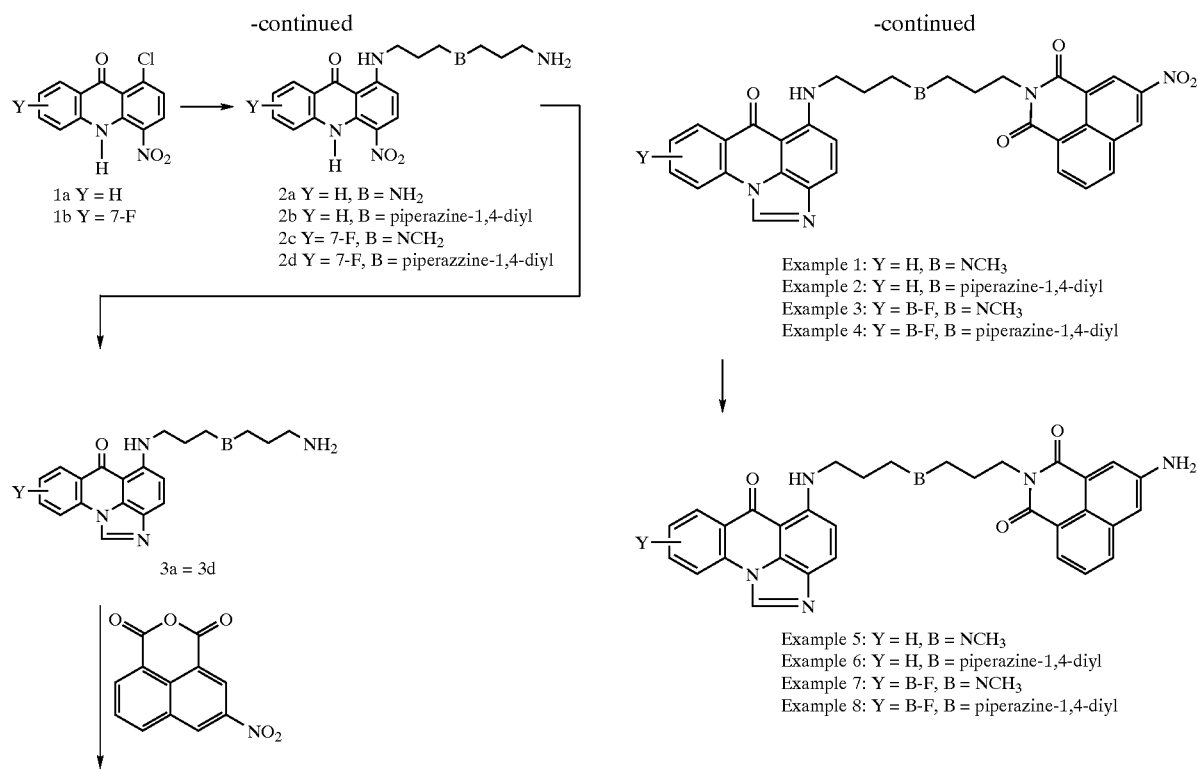

1,8-NAPHTHALIMIDE IMIDAZO{4,5,1-DE}ACRIDONES WITH ANTI-TUMOR ACTIVITY

This application claims the benefit of U.S. provisional application Ser. No. 60/187,991 filed Mar. 7, 2000.

FIELD OF THE INVENTION

The present invention relates to the general fields of pharmaceuticals and cancer chemotherapy, particularly to the areas of cytotoxic antitumor agents and DNA intercalating agents. The invention also relates to medicinal chemistry, and the fields of acridone and 1,8-naphthalimide organic chemistry.

BACKGROUND OF THE INVENTION

1. Acridine Intercalators

A number of acridine-based compounds which exhibit antitumor activity have been reported. Cholody et al. described 5-[(amino-alkyl)amino]-imidazo[4,5,1-de] acridin-6-ones as a novel class of antineoplastic agents (Cholody et al., *J. Med. Chem.* 33:49–52 (1990)); 8-substituted 5-[(aminoalkyl)amino]-6H-v-triazolo[4,5,1-de]acridin-6-ones as potential antineoplastic agents (Cholody et al., *J. Med. Chem.* 33:2852–2856 (1990)); and chromophore-modified imidazoacridones and their activity against murine leukemias (Cholody et al., *J. Med. Chem.* 35:378–382 (1992)). Capps et al. described 2-(aminoalkyl)-5-nitropyrazolo[3,4,5-kl]acridines as a new class of anticancer agents (Capps et al., *J. Med. Chem.* 35:4770–4778 (1992)). More recently, an 8-hydroxyimidazo[4,5,1-de] acridin-6-one, C1311, has entered clinical trials (Burger et al., *Br. J. Cancer* 74:1369–1374 (1996); Idem, *Br. J. Cancer* 81:367–375 (1999)).

It is believed that DNA is the primary target for these compounds, and that they bind to DNA by intercalation. There is good evidence that intercalation of DNA by these drugs disrupts the activity of eukaryotic topoisomerase II (Capranico and Zunino, *Eur. J. Cancer* 28A:2055–2060 (1992); Beck et al., *Cancer Chemother. Pharmacol.* 34(Supp):S14–S18 (1994); Nitiss and Beck, *Eur. J. Cancer* 32A:958–966 (1996)).

2. Naphthalimide Intercalators

Braña et al. have described naphthalimides with basic side chains which have anti-tumor activity (Braña et al., *Cancer Chemother. Pharmacol.*, 4:61–66 (1980); *Eur. J. Med. Chem.*, 16:207–212 (1981); U.S. Pat. No. 4,204,063; U.S. Pat. No. 5,183,821). Examples which have reached the clinic include the compounds amonafide (Kornek et al., *Eur. J. Cancer*, 30A:398–400 (1994)) and mitonafide (Rosell et al., *Invest. New Drugs*, 10:171–175 (1992); Llombart et al., ibid., 177–181). Numerous other naphthalimide derivatives, among them nafidimide and azonafide, have been studied as well (Sami et al., *J. Med. Chem.* 39:4978–4987 (1996) and references therein).

3. Acridine and Acridone Bis-intercalators

The strong binding to nucleic acids of bis-intercalators, which contain two planar aromatic systems joined by suitable linker, has long been known (Canellakis et al., *Biochim. Biophys.* Acta 418:277–283 (1976)). Based upon the antitumor activity of the mono-intercalators, which were presumed to function by DNA intercalation, bis-intercalating compounds have been intensely studied as potential antitumor agents. It has been generally assumed that these compounds function by bis-intercalation of both chromophores into DNA.

Chen et al. studied diacridines as potential bifunctional intercalators (Chen et al, *J. Med. Chem.* 21:868–874 (1978)). Gaugain et al. described the synthesis and conformational properties of an ethidium homodimer and an acridine ethidium heterodimer (Gaugain et al., *Biochemistry* 17:5071–5078 (1978)). Sinha et al. described the synthesis and antitumor properties of bis(quinaldine) derivatives (Sinha et al., *J. Med. Chem.* 20:1528–1531(1977)). Roques et al. described the antileukemic activity of pyridocarbazole dimers (Roques et al., *Biochem. Pharmacol.* 28:1811–1815 (1979)). Wright et al. and Le Pecq et al. described bis-intercalating diacridines and the relationship of structure to DNA Binding (Wright et al., *Biochemistry*, 19:5825–5836 (1990); Le Pecq et al., *Eur. J. Biochem.*, 180:359–366 (1989). Pelaprat et al. described 7H-pyridocarbazole dimers as potential antitumor agents (Pelaprat et al., *J. Med. Chem.* 23:1336–1343 (1980)). Cholody et al., disclosed bis (imidazoacridone) derivatives active against colon tumor cells (Cholody et al., *J. Med. Chem.* 38:3043–3052 (1995) and studied the mechanism of action (Hernandez et al., *Cancer Res.* 55:2338–2345 (1995); see also Michejda et al., U.S. Pat. No. 5,508,289 and international application WO 97/38999, the entire disclosures of which are incorporated herein by reference. The same group of workers also disclosed certain bis(triazoloacridone) compounds active against HIV transcription (Turpin et al., *Antimicrob. Agents Chemother.* 42:487–494 (1998).

4. Naphthalimide Bis-intercalators

Braña et al. have described bis-naphthalimides as a class of antitumor agents (Braña et al., *Anti-Cancer Drug Design* 8:257–268 (1993)). Kirshenbaum et al. described DMP-840, a bis-naphthalimide with promising antitumor activity (Kirshenbaum et al. *Cancer Res.* 54:2199–2206 (1994); and Nitiss et al. discussed the mechanism of action of DMP-840 (Nitiss et al., *Biochemistry* 37:3078–3085 (1998)).

Braña et al., in U.S. Pat. Nos. 4,874,863; 5,616,589; and 5,789,418 (all of which are incorporated herein by reference in their entirety), describe numerous bis(1,8-naphthalimide) compounds which have anti-tumor activity. Ardecky described similar acenaphthalene-derived bis-imide intercalators (Ardecky et al, U.S. Pat. No. 5,086,059), as did Cherney and Seitz in U.S. Pat. No. 5,359,070 (both of which are incorporated by reference herein). Cherney et al. have also described benzo- and hetero-fused bis(1,8-naphthalimide) derivatives which have anti-tumor activity (Cherney et al., *Bioorg. Med. Chem. Letters*, 7:163–168 (1997); U.S. Pat. No. 5,585,382, incorporated by reference herein). Braña et al. have also disclosed benzo-fused 1,8-naphthalimides derived from anthracene1,9-dicarboxylic acid (Braña et al., *J. Med. Chem.*, 40:449–454 91997)). Sun et al. have described an extensive series of bis-naphthalimide antitumor agents (Sun et al., WO 92/17453; U.S. Pat. No. 5,206,249; U.S. Pat. No. 5,206,250; U.S. Pat. No. 5,376,664; U.S. Pat. No. 5,488,110; and U.S. Pat. No. 5,641,782, all of which are incorporated herein by reference in their entirety). Weis et al. described bis (1,8-naphthalimide anti-tumor agents having variations in the linker moiety (Weis et al., U.S. Pat. No. 5,604,095, incorporated herein by reference).

5. Structure-activity Relationships in DNA Intercalators

Many factors, such as physico-chemical characteristics of the planar chromophores, nature of the linking chain (length, rigidity, and ionization state), position of attachment, and other factors, strongly influence the binding with DNA and the biological action of these compounds. However, it has been found that although such compounds exhibit high affinity for DNA, there is little correlation between DNA binding affinity and cytotoxicity or antitumor activity. For example, some bis-intercalators are cytotoxic, while closely related compounds are merely cytostatic.

Since structure-activity relationships in the class of bis-intercalators in relation to their in vivo antitumor action remain unclear, it has not been possible to predict which structures will show such activity, even given their binding affinity for DNA. Small structural modifications can substantially alter the pharmacological properties of a DNA intercalator without similarly affecting DNA binding. Accordingly, research is still ongoing to find DNA intercalating compounds with high antineoplastic activity, especially those having selective activity towards specific tumors.

Compounds designed as potential bis-intercalating agents have typically consisted of two identical planar aromatic ring systems ("chromophores") which are capable of intercalation between the base pairs of double-stranded DNA, joined by a flexible linker of suitable length. Compounds having two identical chromophores are referred to herein as "symmetrical". Previous workers in the field have generally assumed that the mechanism of action of bifunctional intercalators depends upon intercalation of both chromophores into DNA (hence the generic term "bis-intercalator"). Bis-intercalated DNA complexes have in fact been observed experimentally (Peek et al., Biochemistry 33:3794–3800 (1994); Shui et al. Curr. Med. Chem. 7:59–71 (2000)).

Accordingly, the design of these agents has most often been based on previous findings concerning structural requirements for bis-intercalation of symmetrical compounds. Most workers have assumed that if a given chromophore is discovered to be a very tight-binding DNA intercalator, then the linking of two such chromophores will generate a superior bifunctional intercalator. Given two identical, linked, tight-binding chromophores, previous workers proceeded to optimize the distance and geometry between the two by modifying the linker, and sought to obtain additional binding interactions between the linker and the DNA.

Thus, once a promising chromophore has been identified, symmetrical bis-intercalators are usually prepared, and attention is focused thereafter on chromophore substituents and on modifications to the linker moiety in attempts to improve anti-tumor activity. There have been a few studies directed at bis(1,8-naphthalimides) which are rendered asymmetric by virtue of differing chromophore substitution, with improvements in solubility and occasional improvements in biological activity being noted (Cherney et al., U.S. Pat. No. 5,359,070, incorporated herein by reference; Idem., Bioorg. Med. Chem. Lett. 7:163–168 (1997); Patten et al., U.S. Pat. No. 5,585,382, incorporated herein by reference). Prior to the present invention, however, there has been very little work directed to substantially unsymmetrical bifunctional intercalators.

BRIEF DESCRIPTION OF THE INVENTION

This invention relates to a novel class of unsymmetrical imidazoacridone-naphthalimide based DNA bifunctional intercalators, and their use as antineoplastic agents. The compounds are 6H-imidazo[4,5,1-de]acridin-6-ones attached through an amino-containing linker at the 5-position to the 2-position of a 1,8-naphthalimide. These compounds, having two different chromophores, have been found to be exceptionally potent anti-tumor agents, superior to symmetrical bifunctional intercalators containing either chromophore alone.

The invention is most broadly directed to (a) compounds of structure 1, (b) methods of their preparation, and (c) methods of treating diseases characterized by excess cellular proliferation, such as cancer, with these compounds. The compounds of the invention have general structure:

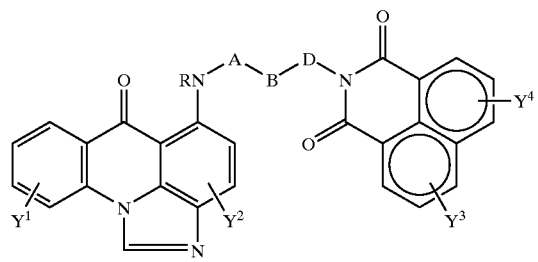

wherein
A=an alkyl linker, such as for example $(CH_2)_m$ or $(CHR)_m$;
B=an amino-containing linker, such as for example NR', NR'$(CH_2)_n$NR'', hexahydropyrimiidine-1,3-diyl, piperazine-1,4-diyl, 4-aminopiperidine-1,4N-diyl, or 1,4-diazacycloheptane-1,4-diyl;
D=an alkyl linker, for example $(CH_2)_p$ or $(CHR)_p$;
Y=any common aromatic substituent, such as for example R, COR, $CO_2R$, CONRR', SR, SOR, $SO_2R$, $SO_2CF_3$, $SO_2NRR'$, OR, $OCF_3$, OCOR, OCONRR', $NO_2$, NRR', CN, Ph, $CF_3$, NRCOR', NRCONR'R'', NRC(NR') NR''R''', $NRCOCF_3$, $NRSO_2R'$, $NRSO_2CF_3$, or halogen;
R=H, $CF_3$, lower alkyl, amino-lower alkyl, or hydroxy-lower alkyl;
R', R''=R, C(O)R, or $SO_2R$; and
m, n, and p=2–6.

DETAILED DESCRIPTION OF THE INVENTION

Figure 1:
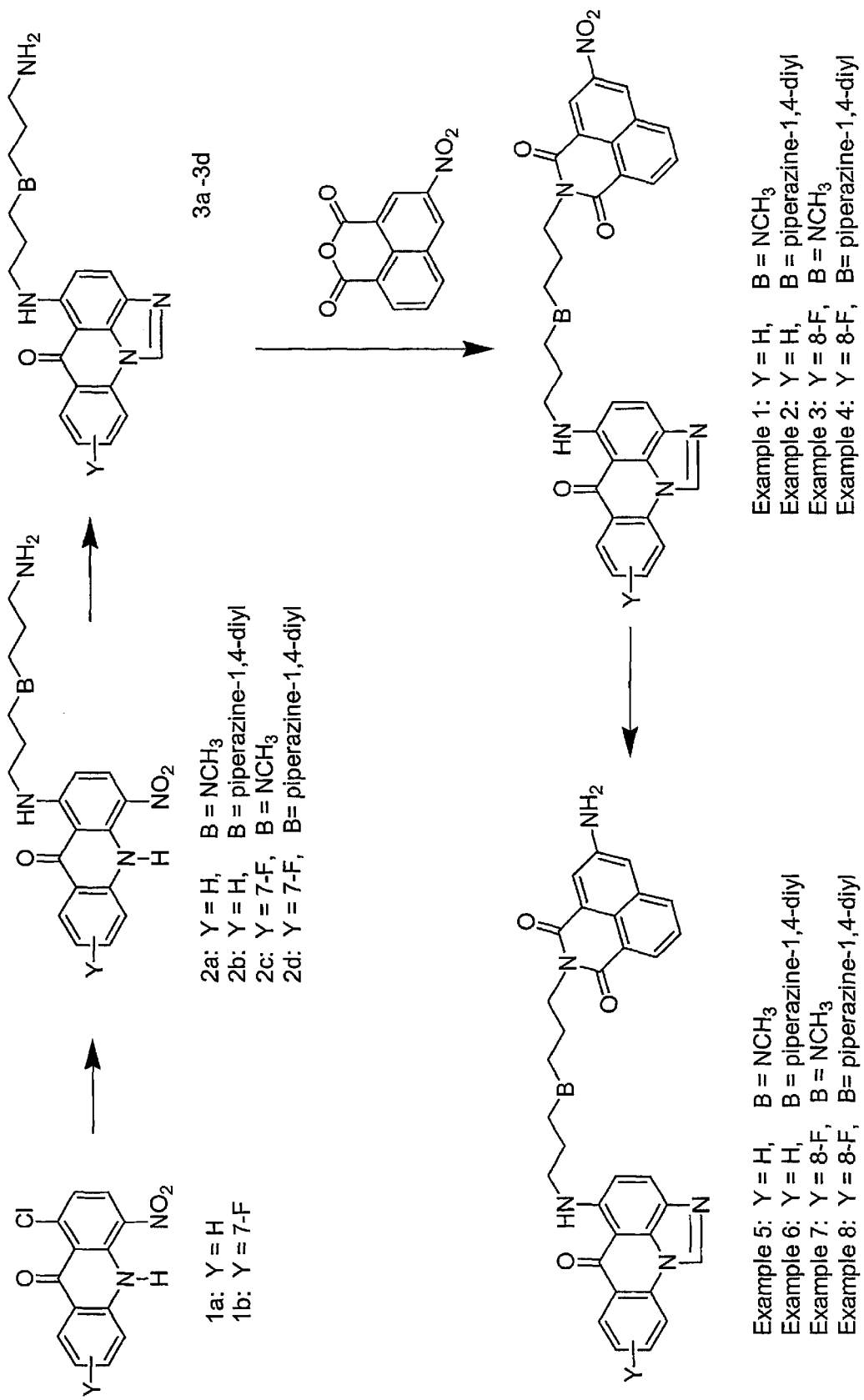
FIG. 1 shows a general synthetic scheme for preparing certain compounds of the invention.

The present inventors have observed, in studies on the physico-chemical interactions of bis-imidazoacridones with DNA, that they do not uniformly bind by bis-intercalation. In addition, it was noted that their biological actions were different from those of ditercalinium, which is a classical bis-intercalator. The results of these studies suggested that while one chromophore of a "bis-intercalator" did indeed intercalate into DNA, the other was unexpectedly interacting with a DNA-binding protein in vivo. It has now been discovered that unsymmetrical "bis-intercalators," referred to herein as "bifunctional intercalators," generally have superior cytostatic, cytotoxic, and anti-tumor activity compared with prior art symmetrical compounds. Specifically, it has been discovered that bifunctional intercalators comprising one 1,8-naphthalimide moiety and one imidazoacridone moiety, connected by an amino-containing linker, are potent anti-tumor agents.

The terms "alkyl" and "acyl" as used herein are intended to include straight-chain, branched, and cyclic alkyl and acyl groups. The terms "lower alkyl" and "lower acyl" refer to such groups having from one to six carbon atoms. For example, n-butyl, t-butyl, and cyclobutyl groups are all encompassed by the term "lower alkyl" as the term is used herein.

The invention more specifically provides compounds of structure:

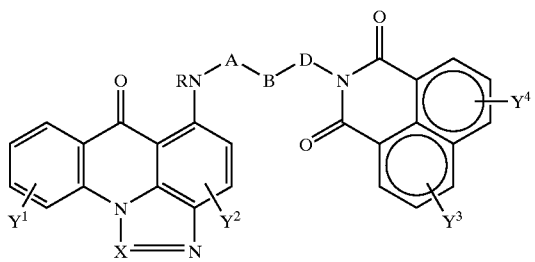

wherein
A=$(CH_2)_m$ or $(CHR)_m$;
B=NR', NR'$(CH_2)_n$NR", hexahydropyrimidine-1,3-diyl, piperazine-1,4-diyl, 4-anminopiperidine-1,4N-diyl, or 1,4-diazacycloheptane-1,4-diyl;
D=$(CH_2)_p$ or $(CHR)_p$;
Y=R, COR, $CO_2R$, CONRR', SR, SOR, $SO_2R$, $SO_2CF_3$, $SO_2NRR'$, OR, $OCF_3$, OCOR, OCONRR', $NO_2$, NRR', CN, Ph, $CF_3$, NRCOR', NRCONR'R", NRC(NR')NR"R'", $NRCOCF_3$, $NRSO_2R'$, $NRSO_2CF_3$, or halogen;
R=H, $CF_3$, lower alkyl, amino-lower alkyl, or hydroxy-lower alkyl;
R', R"=R, C(O)R, or $SO_2R$; and m, n, and p=2–6.

In the above formulation, each occurrence of R, R', and R" is defined independently of any other occurrences in the same molecule; $Y^1-Y^4$ are defined independently of one another; and m, n, and p are independent of one another.

In preferred embodiments, A and D are independently $C_2-C_4$ alkylene, and are optionally substituted with one or more $C_1-C_3$ lower alkyl, hydroxy-lower-alkyl, or amino-lower-alkyl groups; B is chosen from the group consisting of NR, NNRR', $NRCH_2CH_2NR'$, $NRCH_2CH_2CH_2NR'$, and piperazine-1,4diyl; $Y^1-Y^4$ are each independently chosen from the group consisting of R, COR, $CO_2R$, $SO_2R$, $SO_2CF_3$, $SO_2NRR'$, $OCF_3$, $NO_2$, CN, $CF_3$, and halogen; and R is H or lower alkyl.

In particularly preferred embodiments, m, n, and p are independently 2,3, or 4. Another group of particularly preferred compounds are those wherein $Y^3$ is nitro or amino. Yet another group of particularly preferred compounds are those wherein B is piperazine-1,4-diyl. The most preferred compounds are those in which m and p are independently 2,3, or 4 and B is piperazine-1,4-diyl.

With the understanding that the invention is not to be limited by any particular theory of its mechanism of operation, it is hypothesized that the two chromophores, which are necessary for high biological activity and selectivity, play different roles. One provides a mean for docking the drug molecule into specific places on DNA by intercalation, while the second directly interacts with proteins in vivo, specifically with one or more mammalian topoisomerase enzymes.

By the methods provided herein, and by obvious modifications thereto, the compounds of this invention may be prepared from the appropriate starting materials. It is intended that where optical and geometrical isomers are available, the pure isomers and diastereomers, and any and all mixtures thereof, are within the scope of the claims. For example, methods of preparing chiral amino-containing linkers are known in the art or will be obvious to one of ordinary skill in the art. Specific examples are available in the references cited hereinabove. The exemplified compounds, and the methods of their preparation, are presented merely by way of example, and the presentation of selected examples is not intended to limit the scope of the invention.

Another object of this invention is to provide methods of making the compounds of the invention. The compounds may be prepared from commercially available starting materials by the general processes shown below.

In its most general embodiment, one method of preparing the compounds of the invention comprises contacting a compound of structure

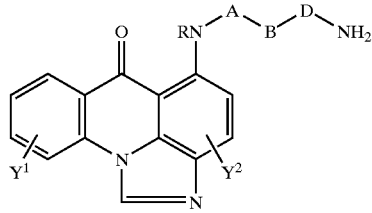

3 with a compound of structure

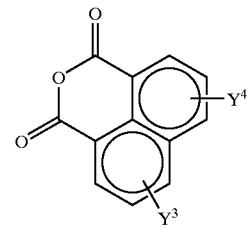

4 in a suitable inert solvent such as DMF, DMSO, NMP, or the like. The time and temperature required for the reaction will vary, depending inter alia upon the nature of D, $Y^3$ and $Y^4$. Generally, the reaction mixture will be gradually raised in temperature until a suitable reaction rate is obtained. This embodiment will be preferred where $Y^3$ and/or $Y^4$ are nitro, halogen, or other readily reducible groups. Specific examples of this embodiment are provided below.

In a second, alternative method of the invention, the following general process is provided, which comprises contacting a compound of structure

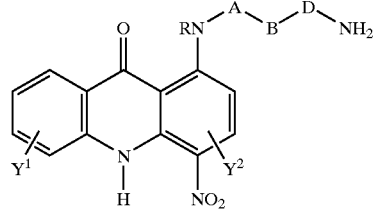

2 with a compound of structure

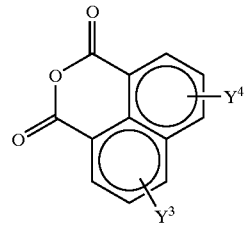

4 in a suitable inert solvent such as DMP, DMSO, NMP, or the like. The time and temperature required for the reaction will again vary, depending inter alia upon the nature of D, $Y^3$ and $Y^4$. Generally, the reaction mixture will be gradually raised in temperature until a suitable reaction rate is obtained.

This particular embodiment further comprises the conversion of the nitro group into a fused imidazolo ring. This may be accomplished by reduction to an amino group, for example by catalytic hydrogenation or transfer hydrogenation, or by chemical reduction with low valent metal species (such as zinc, iron, stannous chloride, or the like), to convert the nitro group into an amino group, followed by condensation with formic acid or a formate ester or orthoester. Preferably, both operations are carried out simultaneously, by catalytic transfer hydrogenation in the presence of formate or formic acid as exemplified herein:

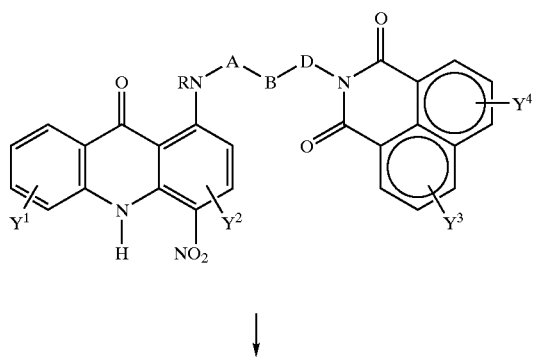

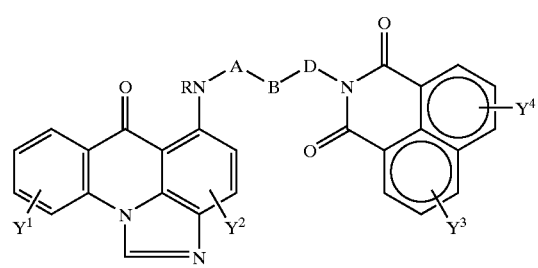

Alternatively, in a third method of the invention, the following general process is provided, which comprises contacting a compound of structure

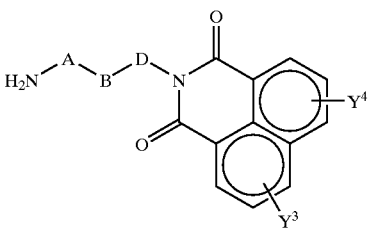

5 with a compound of structure

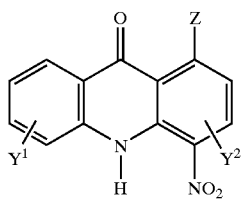

1 wherein Z is F, Cl, or another leaving group, in a suitable inert solvent such as DMF, DMSO, NMP, or the like. The time and temperature required for the reaction will again vary, depending inter alia upon the nature of Z, $Y^1$ and $Y^2$. Generally, the reaction mixture will be gradually raised in temperature until a suitable reaction speed is obtained. This embodiment also requires subsequent conversion of the nitro group into a fused imidazole ring, which may be accomplished as described above.

Compounds where at least one substituent Y is nitro may be converted to compounds where that substituent is amino, by reductive methods well-known in the art, such as catalytic hydrogenation and reduction with low-valent metal species such as Sn(II), Zn(0), Fe(0), and the like. Likewise, compounds where at least one substituent Y is benzloxy or benzyloxycarbonyloxy can be converted to compounds where that substituent is hydroxy, by hydrogenolysis methods known in the art. Alternatively, Y may be OH throughout the synthetic transformations.

In general, it is anticipated that any of the various 1,8-naphthalimide moieties, any of the various amino-containing linkers, and any of the various imidazoacridone moieties which are known as components of DNA intercalators, can be combined into compounds of the present invention. It is further anticipated that such combinations will for the most part be capable of intercalating into DNA, and that the majority of such intercalating combinations will be capable of inhibiting topoisomerase activity. Accordingly, all such compounds are conceived of as being within the scope of the invention.

The starting heterocyclic systems required for these preparative methods are either commercially available, or readily prepared by known synthetic methods. For example, 1,8-naphthalic anhydride is commercially available, and there are published methods for preparation of various substituted derivatives. Similarly, numerous published methods for preparation of imidazo[4,5,1-de]acridones are available. Representative detailed procedures of the methods of synthesis are provided in the examples below.

Another object of this invention is to provide a method of treating a mammal suffering from cancer, or another disease characterized by undesirable cell proliferation, with the compounds of the invention. The method of the invention comprises administering to an individual mammal a therapeutically effective amount of at least one compound of formula

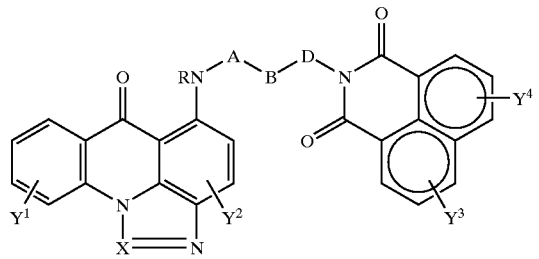

or a prodrug or pharmaceutically acceptable salt thereof, which is sufficient to inhibit the undesired cell proliferation or tumor growth.

The dose of the compound used in the treatment of such disease will vary in the usual way with the weight and metabolic health of the patient, the severity of any side-effects, and the relative efficacy of the compound employed when used against the type of tumor involved. The preferred initial dose for the general patient population will be determined by routine dose-ranging studies, as are conducted for example during clinical trials. Therapeutically effective doses for individual patients may be determined by titrating the amount of drug given to the individual to arrive at the desired therapeutic effect without incurring an unacceptable level of side effects, as is currently and routinely done with other forms of chemotherapy.

For example, a preferred initial dose may be estimated to be between about 10 and 2000 mg/day for an adult human, more preferably between 100 and 1000 mg/day. The initial dose may be varied so as to obtain the optimum therapeutic effect in the patient, and may be provided as a daily dose, in a divided dose regimen, or by continuous infusion.

Administration of the compounds of this invention may be by any method used for administering therapeutics, such as for example oral, parenteral, intravenous, intramuscular, subcutaneous, or rectal administration.

This invention also provides pharmaceutical compositions useful for providing anti-tumor activity, which comprise at least one compound of the invention. In addition to comprising at least one of the compounds described herein, or a pharmaceutically acceptable addition salt or pro-drug thereof, the pharmaceutical composition may also comprise additives such as preservatives, flavorants, excipients, fillers, wetting agents, binders, disintegrants, buffers, and/or carriers. Suitable additives may be for example magnesium and calcium carbonates, carboxymethylcellulose, starches, sugars, gums, magnesium or calcium stearate, coloring or flavoring agents, and the like. There exists a wide variety of pharmaceutically acceptable additives for pharmaceutical dosage forms, and selection of appropriate additives is a routine matter for those skilled in art of pharmaceutical formulation.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose. Unit dose forms for oral administration may be tablets, capsules, and the like, and may contain conventional excipients such as binding agents, for example syrup, acacia, gelatin, sorbitol, tragacanth, or polyvinylpyrrolidone; and carriers or fillers, for example lactose, sugar, maize-starch, calcium phosphate, sorbitol or glycine. Additives may include disintegrants, for example starch, polyvinylpyrrolidone, sodium starch glycolate or microcrystalline cellulose; preservatives, and pharmaceutically acceptable wetting agents such as sodium lauryl sulfate.

In addition to unit dose forms, multi-dosage forms are also contemplated to be within the scope of the invention. Delayed-release compositions, for example those prepared by employing slow-release coatings, micro-encapsulation, and/or slowly-dissolving polymer carriers, will also be apparent to those skilled in the art, and are contemplated to be within the scope of the invention. For example, the compounds of this invention may be incorporated into biodegradable polymers allowing for sustained release, the resulting compositions preferably being implanted where delivery is desired, for example, at the site of a tumor. Biodegradable polymers suitable for this embodiment are well-known in the art, see for example Brem et al., *J. Neurosurg.* 74:441–446 (1991). The compounds of this invention may be also be incorporated into other sustained-release formulations, such as those employing coated particles. See for example U.S. Pat. No. 5,968,551 (which is incorporated by reference herein) and references therein.

The solid oral compositions may be prepared by conventional methods of blending, filling, tabletting or the like. Repeated blending operations may be used to distribute the active agent throughout those compositions employing large quantities of fillers. Such operations are conventional in the art. The tablets may be coated according to methods well known in normal pharmaceutical practice, for example with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, and hydrogenated edible fats; emulsifying agents, for example lecithin, sorbitan monooleate, or acacia; non-aqueous vehicles (which may include edible oils), for example almond oil or fractionated coconut oil, oily esters such as esters of glycerin, propylene glycol, or ethyl alcohol; preservatives, for example methyl or propyl p-hydroxybenzoate or sorbic acid; and if desired conventional flavoring or coloring agents.

For parenteral administration, which will be a preferred route of administration in the hospital or cancer clinic environment, fluid unit dosage forms are prepared utilizing the compound and a sterile vehicle. Depending on the concentration used, the compound can be either suspended or dissolved in the vehicle. In preparing solutions the compound can be dissolved in water or saline for injection and filter sterilized before filling into a suitable vial or ampoule and sealing. Advantageously, additives such as a local anaesthetic, a preservative and buffering agents can be dissolved in the vehicle. Suitable buffering agents are, for example, phosphate and citrate salts. To enhance the stability, the composition can be frozen after filling into the vial and the water removed under vacuum.

Parenteral suspensions are prepared in substantially the same manner, except that the compound is suspended in the vehicle instead or being dissolved, and sterilization accordingly cannot readily be accomplished by filtration. The compound can be sterilized by filtration of an alcohol solution, or by other conventional means, for example by exposure to radiation before or after being suspended in the sterile vehicle. Advantageously, a surfactant or wetting agent is included in the composition to facilitate uniform distribution of the compound and stability of the suspension.

All references cited in this disclosure are incorporated by reference herein, in their entirety.

EXAMPLES

1. Synthesis of Compounds

Commercial reagents were purchased from Aldrich Chemical Company (Milwaukee, Wis.). All commercial solvents and reagents were used without further purification. Column chromatography was performed on 70–230 mesh silica gel. Melting points were determined on an Electrothermal capillary melting point apparatus and are uncorrected. $^1$H NMR spectra were recorded on a Varian VXR-S spectrometer operating at 500 MHz, using TMS as an internal standard. Elemental analyses were within ±0.4% of theoretical values for C, H, and N. Starting materials may be prepared according to, or in analogy to, various published procedures. See for example Capps et al., EP application 145226 (1985); Tarasov et al., *Photochem. Photobiol.* 70:568–578 (1999); Cholody et al., *J. Med. Chem.* 38:3043–3052 (1995); Idem., EP Application 0502668 (1992); Michejda et al., U.S. Pat. No. 5,508,289; Michejda et al., PCT application WO97/38999 (1997); and other documents referenced herein.

6-Chloro-2-[(4-Fluorophenyl)Amino]-3-nitrobenzoic Acid

A mixture of 2,6-dichloro-3-nitrobenzoic acid (18.88 g, 0.08 mol), 4-fluoroaniline (26.8 g, 0.18 mol) and EtOH (50 ml) was refluxed for 30 hours. The solvent was evaporated, benzene (100 ml) and 2N aqueous NaOH (150 ml) were added to the residue, and the mixture was vigorously stirred for 1 hour. Undissolved material was separated by filtration, the aqueous layer was isolated, and traces of benzene were removed by partial evaporation. The solution was then made acidic by addition of concentrated hydrochloric acid. The resulting yellow precipitate was collected by filtration and washed with water (100 ml). After drying, the crude material was crystallized from toluene to give 15.36 g (62%) of 7: mp 216–220° C. Anal. ($C_{13}H_7N_2O_4ClF$) C, H, N.

By this method, beginning with the appropriate anilines, the following compounds can also be prepared:

6-chloro-2-(4-methylphenyl)amino-3-nitro-benzoic acid,
6-chloro-2-(4-methoxyphenyl)amino-3-nitrobenzoic acid,
6-chloro-2-(4-benzyloxyphenyl)amino-3-nitrobenzoic acid,
6-chloro-2-(3-methylphenyl)amino-3-nitrobenzoic acid,
6-chloro-2-(3-methoxyphenyl)amino-3-nitrobenzoic acid,
6-chloro-2-(4-cyanophenyl)amino-3-nitrobenzoic acid,
6-chloro-2-(3-cyanophenyl)amino-3-nitrobenzoic acid,
6-chloro-2-[4-(methoxycarbonyloxy)phenyl]amino-3-nitrobenzoic acid,
6-chloro-2-[4-(methanesulfonyl)phenyl]amino-3-nitrobenzoic acid,
6-chloro-2-[4-(trifluoromethoxy)phenyl]amino-3-nitrobenzoic acid,
and others.

1-Chloro-7-Fluoro4-nitro-10H-acridin-9-one (1b)

A mixture of 6-chloro-2-[(4-fluorophenyl)amino]-3-nitrobenzoic acid (12.39 g, 0.04 mol), chloroform (100 ml), and POCl$_3$ (60 ml, 0.64 mol) was stirred at reflux for 8 h. Solvents were removed under reduced pressure. To the residue was added 200 ml of a mixture of 1,4-dioxane and water (8:1), and the mixture was acidified with concentrated hydrochloric acid and stirred at reflux for 2 h. Water was added (200 ml) and the precipitate was collected by filtration and crystallized from N,N-dimethylformamide—water to give 10.2 g (87%) of 1b as orange needles: mp 287–291° C. Anal. ($C_{13}H_6N_2O_3ClF$) C, H, N.

By this method, but starting with the appropriate 6-chloro-2-arylamino-3-nitrobenzoic acids, and separating isomers by recrystallization and/or column chromatography where needed, the following can be prepared:

1-chloro-7-methyl-4-nitro-10H-acridin-9-one,
1-chloro-7-methoxy-4-nitro-10H-acridin-9-one,
1-chloro-7-benzyloxy-4-nitro-10H-acridin-9-one,
1-chloro-6-methyl-4-nitro-10H-acridin-9-one,
1-chloro-6-methoxy-4-nitro-10H-acridin-9-one,
1-chloro-7-cyano-4-nitro-10H-acridin-9-one,
1-chloro-6-cyano-4-nitro-10H-acridin-9-one,
1-chloro-7-methoxycarbonyloxy-4-nitro-10H-acridin-9-one,
1-chloro-7-methanesulfonyl-4-nitro-10H-acridin-9-one,
1-chloro-7-trifluoromethoxy-4-nitro-10H-acridin-9-one,
and others.

1-{3-[4-(3-Aminopropyl)Piperazin-1-yl]propyl}Amino-7-fluoro-4-nitro-10H-acridin-9-one. (Compound 2d)

A mixture of 1-chloro-7-fluoro-4-nitro-10H-acridin-9-one (2.93 g, 0.01 mol), N,N-dimethylformamide (50 ml), and 1,4-bis(3-aminopropyl)piperazine (10.0 g, 0.05 mol) was stirred at room temperature for 20 hours. Water (250 ml) was added, and the reaction mixture was stirred thoroughly and left overnight in a refrigerator. The fine precipitate was collected by centrifugation, transferred into 2% hydrochloric acid (300 ml), and stirred for 2 hours. Undissolved material was separated by centrifugation. The solution was made alkaline and the product was extracted with chloroform (3×100 ml). The chloroform extract was dried and evaporated. Crude product was crystallized from toluene-hexane to give 2.78 g (61%) of 2d as a yellow solid: mp 130–134° C. Anal. ($C_{23}H_{29}N_6O_3F$) C, H, N.

Beginning with N,N-bis(3-aminopropyl)methylamine, 1-{3-[methyl(3-aminopropyl)amino]propyl}amino-7-fluoro-4-nitro-10H-acridin-9-one (compound 2c) is prepared by the above method. By the same method, but beginning with 1,4-bis(2-aminoethyl)piperazine, it is possible to prepare 1-{2-[4-(2-aminoethyl)piperazin-1-yl]ethyl}amino-7-fluoro-4-nitro-10H-acridin-9-one.

5-{3-[4-(3-Aminopropyl)Piperazin-1-yl]propyl}Amino-8-fluoro-6H-imidazo[4,5,1-de]Acridin-6-one (Compound 3d)

A solution of 2d (1.37 g, 0.003 mol) in 88% formic acid (30 ml) was hydrogenated over Raney nickel (0.8 g) under H$_2$ at 1 atm overnight. The reaction mixture was filtered to remove the catalyst. To the filtrate concentrated hydrochloric acid (3 ml) was added and the mixture was stirred at reflux for 8 hours. The reaction mixture was concentrated to about 10 ml and the product was precipitated as a salt by addition of acetone (50 ml). After drying the precipitate was dissolved in water (10 ml) and chromatographed on a preparative HPLC reverse phase column with a gradient of 0.5% TFA in water:methanol (95:5 to 40:60). The major fraction was collected and made alkaline, and the product was extracted with chloroform (3×100 ml). After evaporation of solvent the product was crystallized from benzene-hexane to give 0.741 g (59%) of 3d as a yellow crystalline powder: mp 126–130° C.; $^1$H NMR (CDCl$_3$) 8.99 (t, 1H), 8.50 (s, 1H), 8.20 (m, 1H), 7.97 (d, 1H), 7.92 (m, 1H), 7.52 (m, 1H, C9-H), 6.81 (d, J=9.0 Hz, 1H, C4-H), 3.50 (m, 2H), 2.75 (t, 2H), 2.52 (m, 10H), 2.42 (t, 2H), 1.96 (m, 2H), 1.65 (m, 2H). Anal. ($C_{24}H_{29}N_6OF$) C, H, N.

General Procedure for the Preparation of Examples 1–4

A mixture of 3-nitro-1,8-naphthalenedicarboxylic anhydride (0.001 mol) and the, appropriate amine 3 (0.001 mol) is stirred at 80° C. in dimethylformamide (8 ml) until the reaction is complete by TLC. The precipitated solid is filtered, washed, and dried, and may be purified by column chromatography or by crystallization to yield the following compounds. By similar methods, various other substituted 1,8-naphthalene-dicarboxylic anhydrides may be converted into analogous compounds.

Example 1

5-{3-{N-[3-(1,3-dioxo-5-nitro-1H-benz[de]
isoguinolin-2-yl)propyl]-
methylamino}propyl}amino}-6H-imidazo[4.5.1-de]
Acridin-6-one Purified by silica gel column chromatography using chloroform-methanol (8:1) mixture as eluent: yield 74%, mp 218–221 ° C.; $^1$H NMR (CDCl$_3$) 9.23 (d, 1H), 9.04 (d, 1H), 8.97 (t, 1H), 8.71 (m, 1H), 8.50 (s, 1H), 8.34 (m, 1H), 7.94 (d, 1H), 7.88 (m, 2H), 7.77 (m, 1H), 7.49 (m, 1H), 6.77 (d, 1H), 4.27 (m, 2H), 3.50 (qt, 2H), 2.56 (t, 4H), 2.30 (s, 3H), 1.95 (m, 4H). Anal. ($C_{33}H_{28}N_6O_5$) C, H, N.

Example 2

5-{3-{4-[3-(1,3-Dioxo-5-nitro-1H-benz[de]
isoguinolin-2-yl)propyl]-piperazin-1-
yl}propyl}amino}-6H-imidazo[4,5,1-de]acridin-6-
one Orange crystals after crystallization from dimethylformamide-water: yield 82%, mp 227–230° C.; $^1$H NMR (CDCl$_3$) 9.31 (d, 1H), 9.13 (d, 1H), 8.97 (t, 1H), 8.76 (m, 1H), 8.56 (m, 1H), 8.55 (s, 1H), 8.42 (m, 1H), 7.94 (m, 3H), 7.89 (m, 1H), 7.54 (m, 1H), 6.78 (d, 1H), 4.29 (m, 2H), 3.45 (qt, 2H), 2.53 (t, 2H), 2.48 (br m, 4H), 2.39 (t, 2H), 2.34 (br m, 4H), 1.96 (m, 2H), 1.88 (m, 2H). Anal. ($C_{36}H_{33}N_7O_5$) C, H, N.

Example 3

5-{3-{N-[3-(1,3-dioxo-5-nitro-1H-benz[de]
isoguinolin-2-yl)propyl]-
methylamino}propyl}amino}-8-fluoro-6H-imidazo
[4,5,1-de]acridin-6-one A mixture of 3-nitro-1,8-naphthalenedicarboxylic anhydride (0.001 mol) and the amine 3c (0.001 mol) is stirred at 80° C. in dimethylformarnide (8 ml) until the reaction is complete by TLC. The precipitated solid is filtered, washed, dried and purified by column chromatography.

Example 4

5-{3-{4-[3-(1,3-Dioxo-5-nitro-1H-benzrde]
isoguinolin-2-yl)propyl]-piperazin-1-
yl}propyl}amino}-8-fluoro-6H-imidazo[4,5,1-de]
acridin-6-one Crystallized twice from dimethylformamide-water: yield 69%, mp 238–240 ° C.; $^1$H NMR (CDCl$_3$) 9.31 (d, 1H), 9.13 (d, 1H), 8.96 (t, 1H), 8.78 (m, 1H), 8.51 (s, 1H), 8.43 (m, 1H), 8.22 (m, 1H), 7.97 (d, 1H), 7.93 (m, 2H), 7.53 (m, 1H), 6.79 (d, 1H), 4.29 (m, 2H), 3.47 (qt, 2H), 2.53 (t, 2H), 2.48 (br m, 4H), 2.39 (t, 2H), 2.34 (br m, 4H), 1.96 (m, 2H), 1.88 (m, 2H). Anal. ($C_{36}H_{32}N_7O_5F$) C, H, N.

Example 5

5-{3-{N-[3-(5-amino-1,3-dioxo-1H-benz[de]
isoguinolin-2-yl)propyl]-
methylamino}propyl}amino}-6H-imidazo[4,5,1-de]
acridin-6-one To a stirred solution of the compound of Example 1 (0.001 mol) in glacial acetic acid (25 ml) is added stannous chloride (1.52 g, 0.008 mol) dissolved in concentrated hydrochloric acid (5 ml). The mixture is stirred at 60 ° C. for 2 h. After cooling, acetone (50 ml) is added and the mixture is stirred vigorously. The precipitate is collected by filtration, washed with acetone, and suspended in water (250 ml). The suspension is made basic (pH~12) with sodium hydroxide and the product is extracted with chloroform (5×50 ml). The crude product is chromatographed on silica gel with a chloroform-methanol (10:1) mixture containing 0.5% isopropylamine to provide the title compound.

Example 6

5-{3-{4-[3-(5-amino-1,3-dioxo-1H-benz[de]
isoguinolin-2-yl)propyl]-piperazin-1
-yl}propyl}amnino}-6H-imidazo[4,5,1-de]acridin-6-
one To a stirred solution of the compound of Example 2 (0.644 g, 0.001 mol) in glacial acetic acid (25 ml), stannous chloride (1.52 g, 0.008 mol) dissolved in concentrated hydrochloric acid (5 ml) was added. The mixture was stirred at 60 ° C. for 2 h. After cooling, acetone (50 ml) was added and the mixture stirred vigorously. The precipitate was collected by filtration, washed with acetone, and suspended in water (250 ml). The suspension was made basic (pH12) with sodium hydroxide and the product was extracted with chloroform (5×50 ml). The crude product was chromatographed on a silica gel column with chloroform-methanol (10:1) mixture containing 0.5% isopropylamine. The main fraction, after evaporation of solvents, gave 0.550 g (89%) of the title compound as a yellow solid: mp 219–222° C.; $^1$H NMR (CDCl$_3$) 8.99 (m, 1H), 8.57 (m, 1H), 8.55 (s, 1H), 8.31 (m, 1H), 8.02 (d, 1H), 7.97 (m, 1H), 7.92 (m, 2H), 7.80 (m, 1H), 7.60 (m, 1H), 7.54 (d, 1H), 7.29 (m, 1H), 6.79 (d, 1H), 4.24 (m, 2H), 4.17 (s, 2H), 3.46 (qt, 2H), 2.51 (t, 2H), 2.48 (br m, 8H), 2.42 (t, 2H), 2.34 (br m, 4H), 1.93 (m, 2H), 1.87 (m, 2H).

Example 7

5-{3-{N-[3-(5-Amino-1,3-dioxo-1H-benz[de]
isoguinolin-2-yl)propyl]-
methylamino}propyl}amino}-8-fluoro-6H-imidazo
[4,5,1-de]acridin-6-one To a stirred solution of the compound of Example 3 (0.001 mol) in glacial acetic acid (25 ml) is added stannous chloride (1.52 g, 0.008 mol) dissolved in concentrated hydrochloric acid (5 ml). The mixture is stirred at 60° C. for 2 h. After cooling, acetone (50 ml) is added and the mixture is stirred vigorously. The precipitate is collected by filtration, washed with acetone, and suspended in water (250 ml). The suspension is made basic (pH~12) with sodium hydroxide and the product is extracted with chloroform (5×50 ml). The crude product is chromatographed on silica gel with a chloroform-methanol (10:1) mixture containing 0.5% isopropylamine to provide the title compound.

Example 8

5-{13-{4-[3-(5-Amino-1,3-dioxo-1H-benz[de] isoquinolin-2-yl)propyl]-piperazin-1-yl}propyl}amino}-8-fluoro-6H-imidazo[4,5,5,1-de] acridin-6-one This compound was obtained by reduction of the compound of Example 4, in an analogous manner to the method of Example 6. Yield: 63% after column chromatography, mp 240–243° C.; $^1$H NMR (CDCl$_3$) 8.78 (m, 1H), 8.51 (s, 1H), 8.31 (m, 1H), 8.22 (m, 1H), 8.02 (d, 1H), 7.97 (m, 1H), 7.92 (m, 2H), 7.60 (m, 1H), 7.29 (d, 1H), 6.79 (d, 1H), 4.24 (m, 2H), 4.16 (s, 2H), 3.46 (qt, 2H), 2.51 (t, 2H), 2.48 (br m, 8H), 2.43 (t, 2H), 2.34 (br m, 4H), 1.94 (m, 2H), 1.88 (m, 2H). Anal. (C$_{36}$H$_{34}$N$_7$O$_3$F) C, H, N.

2. Biological Studies

Cancer Cell Lines. Human colon carcinoma HCT116 and HT29, human melanoma MELSK2, human lung cancer A549, human leukemia HL60 and human breast cancer MCF$_7$ cells were purchased from the American Type Culture Collection (Rockville, Md.). Human pancreatic tumor cell lines 6.03 and 10.05 were a gift from Dr. Elizabeth Jaffe, Johns Hopkins University.

In Vitro Cytotoxicity Studies. Cells were seeded in quadruplicate for each studied concentration in 96-well plates (100 μL of medium containing 2000–2500 cells per well) and were allowed to grow for 24 h (day 0). Stock solutions (2.5 mM) of test compounds were prepared freshly by dissolving their free base forms in distilled water-DMSO (50:50) mixture containing two equivalents of methanesulfonic acid and then diluted in distilled water to the concentration of 500 μM. These solutions were used to prepare 2 μM working solution and its 10-fold serial dilutions in appropriate media. 100 μL of drug containing medium or vehicle (control) was added to each well on day 1. The cytotoxicity was determined using two different methods: the MTT-based, CellTiter96™ Non-Radioactive Cell Proliferation Assay (Promega Inc., Madison, Wis.) according to instructions provided by the manufacturer, and/or the sulforhodamine B (SRB) method (Skehan et al., J. Natl. Cancer Inst. 82:1107–1112 (1990)). At the time at which drugs were added assays were performed on extra reference plates to determine the cell population density at time 0 (T$_0$). After 96 h incubation at 37° C. in a humidified atmosphere containing 5% CO$_2$, the assays were performed on test (T) and control (C) plates. The absorbance of the wells was determined by a Microplate Reader at 540 nm for CellTiter96™ and 490 for SRB. Cellular responses were calculated from the data as described previously: 100×[(T-T$_0$)/(C-T$_0$)] for T>T$_0$ and 100×[(T-T$_0$)/T$_0$] for T<T$_0$. (Monks et al., J. Natl. Cancer Inst. 83:757–766 (1991)). Results are presented in FIGS. 1–4, and as IC$_{50}$ and LC$_{50}$ values in Table 1.

Flow Cytometry Analysis. A suspension of 0.5×10$^6$ cells in 8 ml of medium were placed in 25 cm$^2$ T flask and allowed to attach for 24 h. The cells were then exposed for 6 h to 100 nM of drug . After removal of drug the cells were washed with PBS. Fresh medium (8 ml) was added and incubation at 37° C. in 5% CO$_2$ in complete humidity was continued for an additional five days. At appropriate intervals, treated and control cells were released from flasks by incubation with trypsin (0.05 mg/ml)/EDTA (0.02 mg/ml) for 5 min at 37° C., collected in ice-cold PBS, combined with the removed medium that might contain floating cells, and centrifuged at 4° C. Cell pellets were re-suspended in PBS containing 1% fetal bovine serum. The cells were fixed and stained for fluorescence-activated cell sorting according to standard procedures (Crissman et al., Cytometry 3:84–90(1992)). Fluorescence histograms were obtained on a Coulter EPICS753 Cell Sorter using an argon laser and mean peaks were analyzed.

TABLE 1

Antitumor Activity in Cultured Cells

| | Tumor cell lines | | | | | |
|---|---|---|---|---|---|---|
| Compound | IC$_{50}$ | LC$_{50}$ | IC$_{50}$ | LC$_{50}$ | IC$_{50}$ | LC$_{50}$ |
| | HCT116 | | HT29 | | A549 | |
| Example 1 | 8 | 220 | 25 | 400 | 25 | 500 |
| Example 2 | 0.5 | 32 | 0.9 | 65 | 0.6 | 35 |
| Example 4 | 0.5 | 35 | 1.5 | 35 | 0.6 | 35 |
| Example 6 | 2.2 | 80 | 8 | 750 | 2.5 | 100 |
| Example 8 | 1.8 | 230 | 3.5 | >1000 | 2 | 150 |
| Mitonafide | 250 | >1000 | 300 | >1000 | 65 | 800 |
| | MELSK2 | | HL60 | | MCF7 | |
| Example 1 | 150 | >1000 | 120 | 500 | 50 | >1000 |
| Example 2 | 4 | 60 | 3.5 | 33 | 3.2 | >1000 |
| Example 4 | 4 | 70 | 3.5 | 33 | 3.5 | >1000 |
| Example 6 | 15 | 750 | 5 | 450 | 32 | >1000 |
| Example 8 | 20 | >1000 | 4 | 450 | 46 | >1000 |
| Mitonafide | 150 | 700 | 45 | 400 | 245 | >1000 |

IC50 - drug concentration in nM which causes 50% cell growth inhibition
LC50 - drug concentration in nM which causes 50% cell death Inhibition of DNA synthesis. The effect of test compounds on DNA synthesis was examined by bromodeoxyuridine (BrdU) incorporation using a BrdU Cell Proliferation Assay (Oncogene Research Products, Cambridge, Mass.). In this assay 2,500 cells/well were allowed to attach for 24 h, treated with various concentrations of (hug for 24 h, and then incubated with BrdU for 24 h. The level of incorporated BrdU was measured immunochemically according to the manufacturer's protocol.

Viability assay. Cell death was additionally confirmed by the LIVE/DEAD™ Viability/Cytotoxicity Kit (Molecular Probes, Eugene, Oreg.) applied according to the manufacturer's Fluorescence Microscopy Protocol provided with the kit.

3. Results

Compounds were examined in the NCI 60 human tumor cell line panel (Grever et al., Seminars in Oncology 19:622–638 (1992). In general, the compounds were extremely active. For example, the compound of Example 2 inhibited the growth of all of the tumor cell lines with a median activity in the nanomolar range. The activity of the compounds was examined in greater detail utilizing the MTT cell proliferation assay. This assay indirectly measures the number of living cells by measuring the activity of the mitochondrial dehydrogenase. Briefly, tumor cell cultures, contained in a 96-well plate, are incubated with varying concentrations of the test chemical for various times. At the end of the test period the wells are treated with the MTT dye solution and incubated for 4 hours. Cells which are alive convert the yellow tetrazolium dye into the blue, insoluble formazan product. This precipitate is solubilized, and the absorption at 570 nm is read in an ELISA reader.

Figure 2:
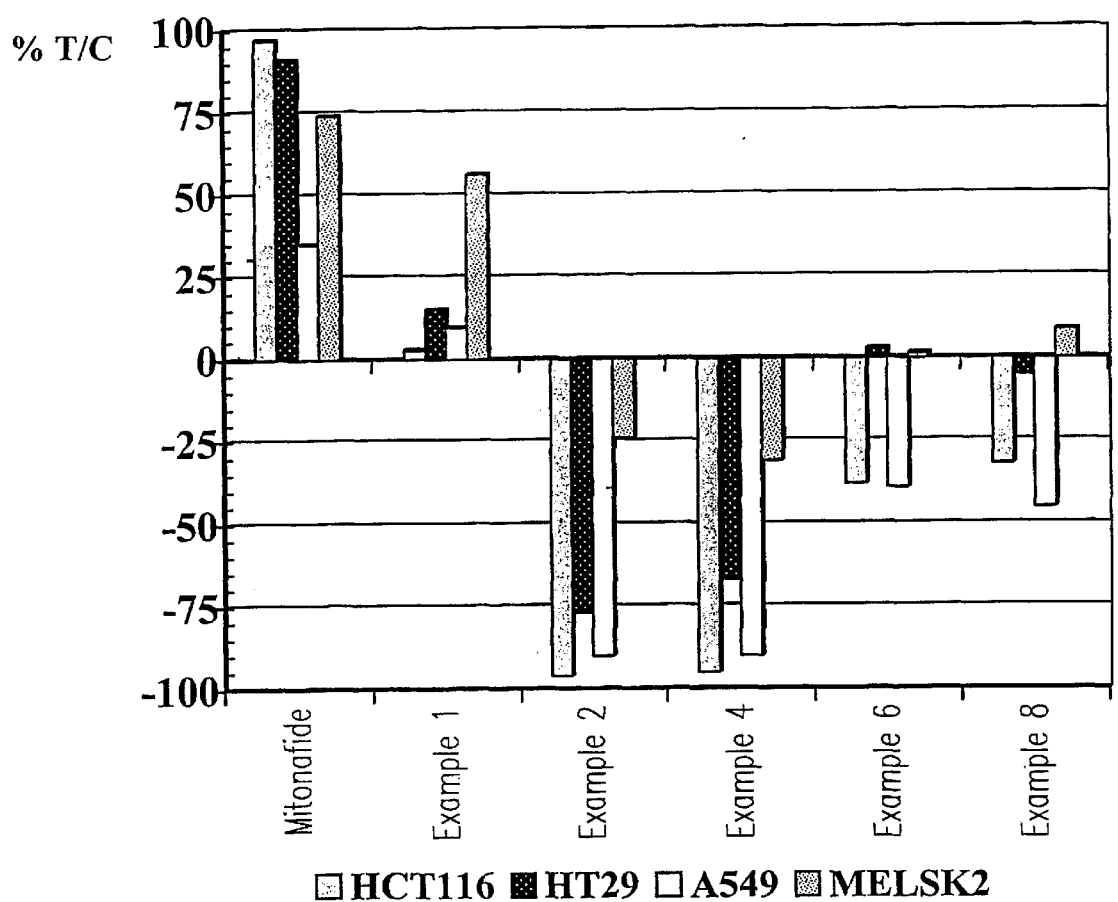
FIG. 2 shows the activity of compounds of the invention against the tumor cell lines HCT116, HT29, A549, and MEL SK2 at a concentration of 100 nM, in the MMT assay.
Figure 3:
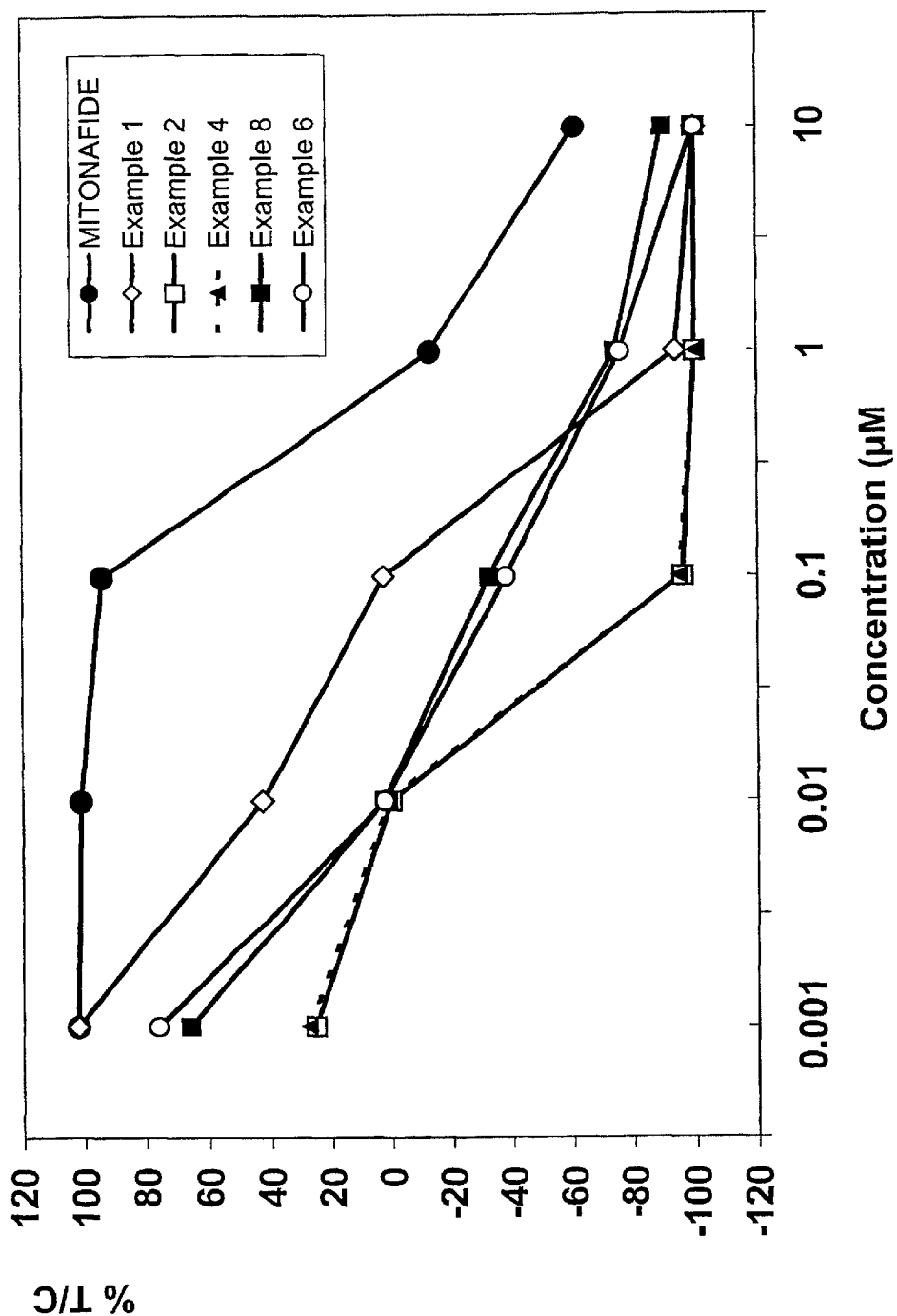
FIG. 3 shows the activity of compounds of the invention against the tumor cell line HCT116 at varying concentrations, in the MMT assay.

FIG. 2 shows the activity of the compounds against two colon tumor cell lines (HCT116 and HT29), the non-small cell lung cancer line A549, and the melanoma line MelSK2, at 100 nM drug concentration. The cells were incubated for 96 hours with the drug. It is clear from the Figure that the melanoma line was less sensitive in general than the other cancers, although the compounds of the invention did produce significant growth arrest. Note that mitonafide, a known agent that contains the nitronaphthalimide moiety, was not very active at this concentration. At the 100 nM concentration the compounds of Examples 2 and 4 exhibited outstanding cytotoxic activity against the three adenocarcinomas. Further in vitro dose-response studies were conducted with the colon line HCT116. FIG. 3 shows the resulting data in graphical form. At concentrations of 1 nM, the compounds of Examples 2 and 4 cause almost complete growth inhibition. Mitonafide did not show this effect until a concentration of 1 $\mu$M was reached. Evidence of induced cytotoxicity with the compounds was seen at 10 nM and, as shown in FIG. 3, substantial killing was observed at 100 nM. These data suggest that the compounds of the invention have potent anti-tumor activity against tumors which are normally difficult to treat.

Figure 4:
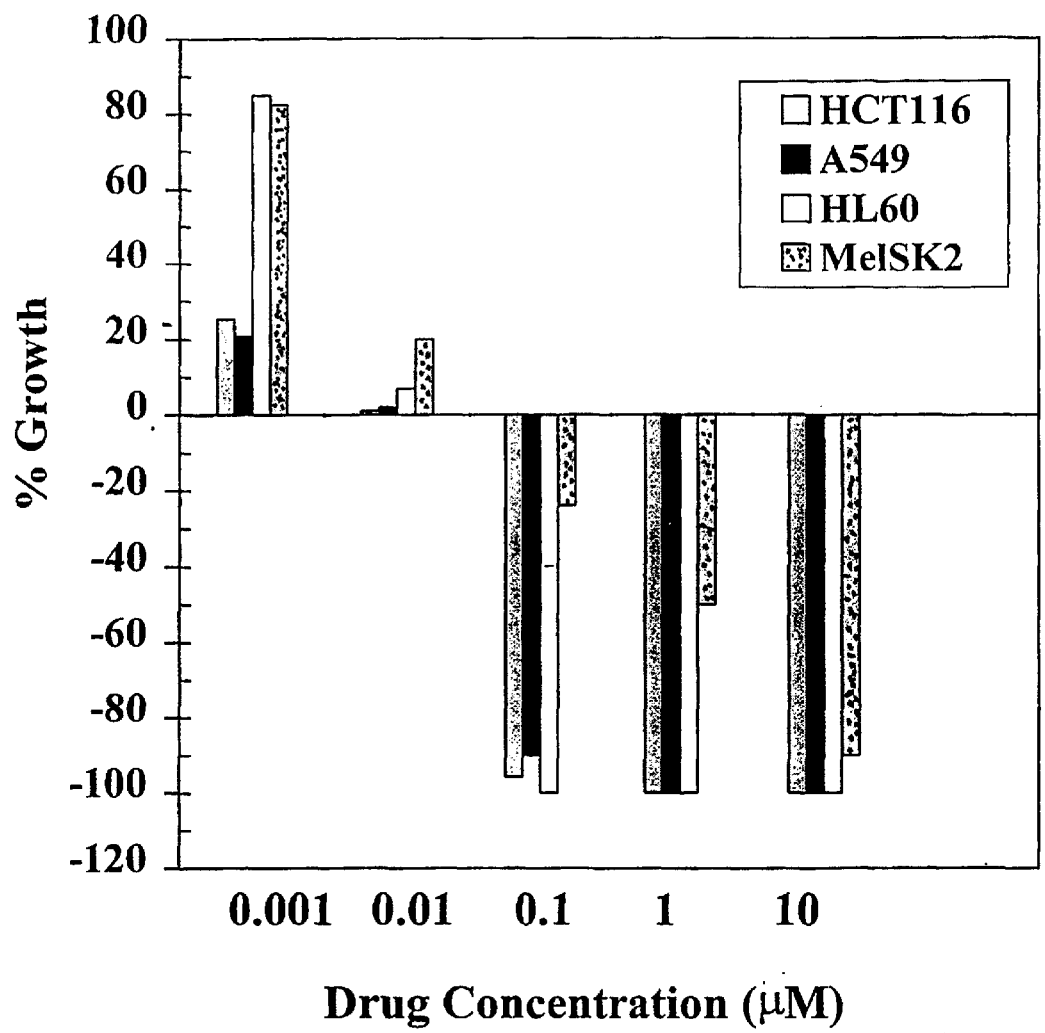
FIG. 4 shows the activity of the compound of Example 2 against the tumor cell lines HCT116, HT29, A549, and Mel.SK2 at varying concentrations, in the SRB assay.

To demonstrate that these data were not dependant on the assay system used, the cytotoxic activity of Example 2 was examined against the four tumor types using the sulforhodamine B (SRB) assay (Skehan et al., *J. Natl. Cancer Inst.* 82:1107–1112 (1990)). FIG. 4 shows the results of this assay, which essentially mirror the results obtained with the MTT end-point.

Figure 5:
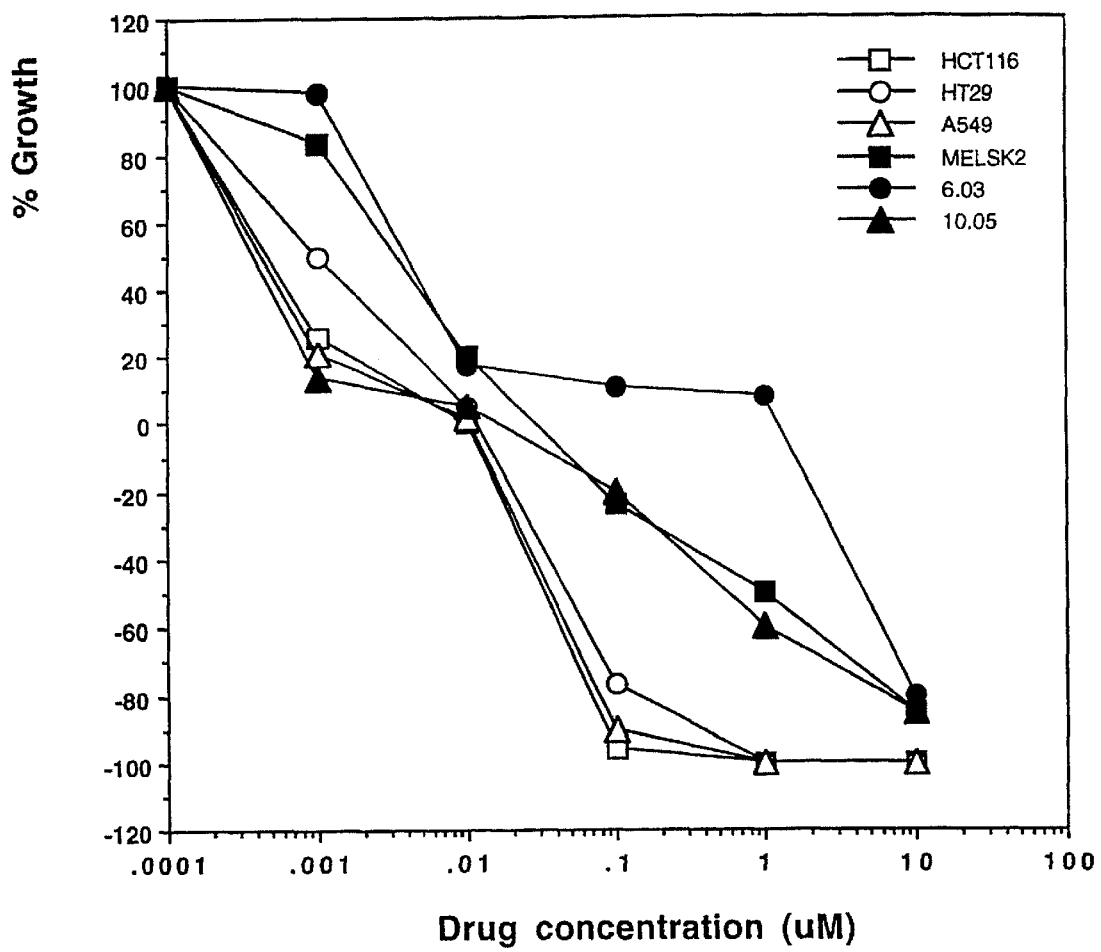
FIG. 5 shows the activity of the compound of Example 2 against the tumor cell lines HCT116, HT29, A549, MEL SK2, 6.03, and 10.5 at varying concentrations, in the SRB assay.

The compound of Example 2 is also potently cytotoxic against extremely refractory pancreatic cancer cell lines. FIG. 5 presents the results of an SRB-based assay on the toxicity of Example 2 against the four cell lines mentioned above, and against two pancreatic cell lines, 6.03 and 10.05 (obtained from Dr. Elizabeth Jaffe, Johns Hopkins University, Baltimore Md.). The compounds were exposed to the agent for 120 hrs. It is clear that both of these lines are sensitive to the compound. The more resistant line 6.03, becomes growth arrested at 100 nM concentration; the more sensitive line 10.05 suffers substantial cell death at 1 $\mu$M.

In order to determine the mode of cell death induced by the compounds of the invention, the effect of the compound of Example 2 on the cell cycle was studied, utilizing Fluorescence Activated Cell Sorting SACS) analysis. HCT 116 colon cancer cell were treated with the compound of Example 2 for 6 hrs at a concentration of 100 nM, and then allowed to grow in culture for varying times. As early as 24 hrs, the cells became growth arrested at $G_2$-M and some sub-$G_1$ cells began to appear. This fraction, which is associated with apoptotic death, increased steadily with time, and dominated the distribution at 96 hrs. Untreated cells become growth arrested at $G_1$ at 96 hrs as they reach confluence.

Similar cell cycle experiments were carried out on the 10.05 pancreatic cancer line. Dramatic differences were apparent at 48 hrs, and it was clear that substantial apoptosis was occurring at 144 hrs, as evidenced by the growth of the sub-$G_1$ fraction. Similar observations were made with the slower growing 6.03 pancreatic cancer cells, which also showed strong evidence of apoptosis.

The FACS analysis evidence of apoptosis was substantiated by morphological examination of the treated 10.05 pancreatic cancer cells. The treated cells showed evidence of chromatin fragmentation, which was absent in the untreated cells. Similar results were obtained with the 6.03 cells.

The results strongly indicate that the compounds of the invention are potent, selective new cytotoxic agents which are active against tumors that are normally not sensitive to chemotherapeutic agents, and that the unsymmetrical bifunctional intercalators of this invention offer new possibilities for the treatment of cancer.

While the examples presented above describe a number of embodiments of this invention, it is apparent to those skilled in the relevant arts that the compounds, compositions, and methods of this invention can be altered to provide alternative embodiments, and equivalent compositions and methods, which nonetheless remain within the scope of the invention. Therefore, it will be appreciated that the present invention is not limited in scope by the specific embodiments described above, which are merely illustrations of individual aspects of the invention. In particular, modifications which are obvious to those of ordinary skill in the art are intended to be within the spirit and effective scope of the following claims.

We claim:

1. A compound of structure 1:

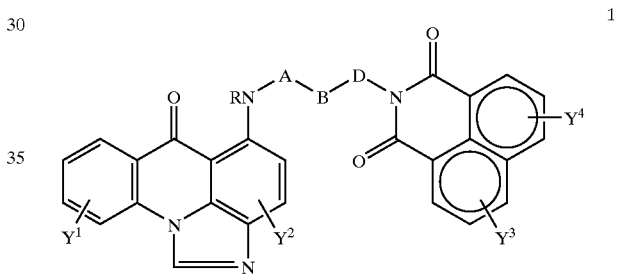

wherein

A is $(CH_2)_m$ or $(CHR)_m$;

B is NR', NR'$(CH_2)_n$NR", hexahydropyrimidine-1,3-diyl, piperazine-1,4diyl, 4-aminopiperidine-1,4N-diyl, or 1,4-diazacycloheptane-1,4-diyl;

D is $(CH_2)_p$ or $(CHR)_p$;

$Y^1$, $Y^2$, $Y^3$ and $Y^4$ are independently R, COR, $CO_2R$, CONRR', SR, SOR, $SO_2R$, $SO_2CF_3$, $SO_2NRR'$, OR, $OCF_3$, OCOR, OCONRR', $NO_2$, NRR', CN, Ph, $CF_3$, NRCOR', NRCONR'R", NRC(NR')NR"R'", $NRCOCF_3$, $NRSO_2R'$, $NRSO_2CF_3$, or halogen;

R is H, $CF_3$, lower alkyl, amino-lower alkyl, or hydroxy-lower alkyl;

R' and R" are independently R, C(O)R, or $SO_2R$; and m, n, and p are independently 2–6.

2. A compound according to claim 1, wherein B is piperazine-1,4-diyl.

3. A compound according to claim 1, wherein $Y^1$, $Y^2$, $Y^3$ and $Y^4$ are independently chosen from the group consisting of H, F, Cl, OR, $NH_2$, $NO_2$, $SO_2CF_3$, CN, and $CF_3$.

4. A compound according to claim 2, wherein $Y^1$, $Y^2$, $Y^3$ and $Y^4$ are independently chosen from the group consisting of H, F, Cl, OR, $NH_2$, $NO_2$, $SO_2CF_3$, CN, and $CF_3$.

5. A compound according to claim 1, selected from the group consisting of:

2-{3-{methyl[3-(6-oxo-6H-imidazo[4,5, 1-de]acridin-5-yl)aminopropyl]amino}propyl}-5-nitro-1H-benz[de]isoquinoline-1,3(2H)-dione;

2-{3-{methyl[3-(8-fluoro-6-oxo-6H-imidazo[4,5,1-de]acridin-5-yl)aminopropyl]-amino}propyl}-5-nitro-1H-benz[de]isoquinoline-1,3(2H)-dione;

2-{3-{methyl[3-(8-hydroxy-6-oxo-6H-imidazo[4,5,1-de]acridin-5-yl)aminopropyl]-amino}propyl}-5-nitro-1H-benz[de]isoquinoline-1,3(2H)-dione;

2-{3-{methyl[3-(8-trifluoromethyl-6-oxo-6H-imidazo[4,5,1-de]acridin-5-yl)aminopropyl]amino}propyl}-5-nitro-1H-benz[de]isoquinoline-1,3(2H)-dione;

2-{3-{methyl[3-(6-oxo-6H-imidazo[4,5,1-de]acridin-5-yl)aminopropyl]amino}propy}-5-amino-1H-benz[de]isoquinoline-1,3(2H)-dione:

2-{3-{methyl[3-(8-fluoro-6-oxo-6H-imidazo[4,5,1-de]acridin-5-yl)aminopropyl]-amino}propyl}-5-amino-1H-benz[de]isoquinoline-1,3(2H)-dione;

2-{3-{methyl[3-(8-hydroxy-6-oxo-6H-imidazo[4,5,1-de]acridin-5-yl)aminopropyl]-amino}propyl}-5-amino-1H-benz[de]isoquinoline-1,3(2H)-dione; and 2-{3-{methyl[3-(8-trifluoromethyl-6-oxo-6H-imidazo[4,5,1-de]acridin-5-yl)aminopropyl]amino}propyl}-5-amino-1H-benz[de]isoquinoline-1,3(2H)-dione.

6. A compound according to claim 2, selected from the group consisting of:

2-{3-{4-[3-(6-oxo-6H-imidazo[4,5,1-de]acridin-5-yl)aminopropyl]piperazin-1-yl}propyl}-5-nitro-1H-benz[de]isoquinoline-1,3(2H)-dione;

2-{3-{4-[3-(8-fluoro-6-oxo-6H-imidazo[4,5,1-de]acridin-5-yl)aminopropyl]piperazin-1-yl}propyl}-5-nitro-1H-benz[de]isoquinoline-1,3(2H)-dione;

2-{3-{4-[3-(8-hydroxy-6-oxo-6H-imidazo[4,5,1-de]acridin-5-yl)aminopropyl]-piperazin-1-yl}propyl}-5-nitro-1H-benz[de]isoquinoline-1,3(2H)-dione;

2-{3-{4-[3-(8-trifluoromethyl-6-oxo-6H-imidazo[4,5,1-de]acridin-5-yl)aminopropyl]piperazin-1-yl}propyl}-5-nitro-1H-benz[de]isoquinoline-1,3(2H)-dione;

2-{3-{4-[3-(6-oxo-6H-imidazo[4,5,1-de]acridin-5-yl)aminopropyl]piperazin-1-yl}propyl}-5-amino-1H-benz[de]isoquinoline-1,3(2H)-dione;

2-{3-{4-[3-(8-fluoro-6-oxo-6H-imidazo[4,5,1-de]acridin-5-yl)aminopropyl]piperazin-1-yl}propyl}-5-amino-1H-benz[de]isoquinoline-1,3(2H)-dione;

2-{3-{4-[3-(8-hydroxy-6-oxo-6H-imidazo[4,5,1-de]acridin-5-yl)aminopropyl]piperazin-1-yl}propyl}-5-amino-1H-benz[de]isoquinoline-1,3(2H)-dione; and 2-{3-{4-[3-(8-trifluoromethyl-6-oxo-6H-imidazo[4,5,1-de]acridin-5-yl)aminopropyl]piperazin-1-yl}propyl}-5-amino-1H-benz[de]isoquinoline-1,3(2H)-dione.

7. A method of preparing a compound according to claim 1, comprising the step of contacting a compound of structure

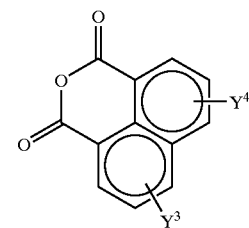

with a compound of structure

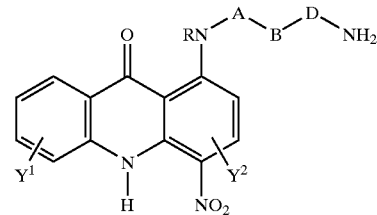

in a suitable inert solvent.

8. A method of preparing a compound according to claim 1, comprising the step of contacting a compound of structure

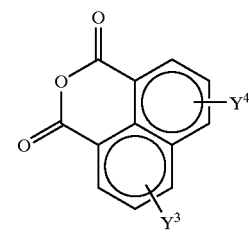

with a compound of structure

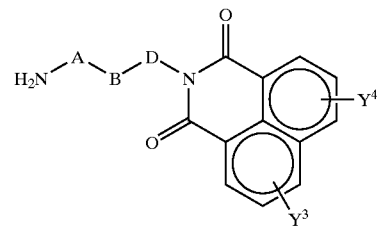

in a suitable inert solvent.

9. A method of preparing a compound according to claim 1, comprising the step of contacting a compound of structure

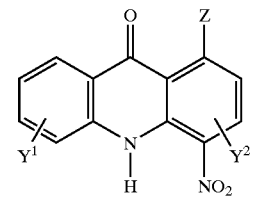

with a compound of structure

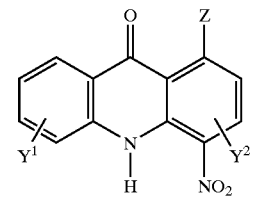

wherein Z is F, Cl, or another leaving group, in a suitable inert solvent.

10. A method of inhibiting the proliferation of mammalian cells, comprising exposing said cells to an effective amount of a compound of claim 1.

11. A method of inhibiting the proliferation of mammalian cells, comprising exposing said cells to an effective amount of a compound of claim 2.

12. A method of inhibiting growth of a tumor, comprising exposing said tumor to an effective amount of a compound of claim 1.

13. A method of inhibiting growth of a tumor, comprising exposing said tumor to an effective amount of a compound of claim 2.

14. The method of claim 12, wherein the tumor is an adenocarcinoma.

15. The method of claim 13, wherein the tumor is an adenocarcinoma.

16. A method of treating a mammal suffering from cancer, comprising administering to said mammal an effective amount of a compound of claim 1, or a pharmaceutically acceptable salt thereof.

17. A method of treating a mammal suffering from cancer, comprising administering to said mammal an effective amount of a compound of claim 2, or a pharmaceutically acceptable salt thereof.

18. A pharmaceutical composition comprising an effective amount of a compound of claim 1, or a pharmaceutically acceptable salt thereof, further comprising one or more pharmaceutically acceptable additives selected from the group consisting of carriers, preservatives, flavorants, excipients, fillers, wetting agents, binders, disintegrants, and buffers.

19. A pharmaceutical composition comprising an effective amount of a compound of claim 2, or a pharmaceutically acceptable salt thereof, further comprising one or more pharmaceutically acceptable additives selected from the group consisting of carriers, preservatives, flavorants, excipients, fillers, wetting agents, binders, disintegrants, and buffers.

20. A pharmaceutical composition comprising an effective amount of a compound of claim 3, or a pharmaceutically acceptable salt thereof, further comprising one or more pharmaceutically acceptable additives selected from the group consisting of carriers, preservatives, flavorants, excipients, fillers, wetting agents, binders, disintegrants, and buffers.

* * * * *